United States Patent [19]

Cedro et al.

[11] Patent Number: 5,948,405
[45] Date of Patent: Sep. 7, 1999

[54] FUCANS WITH LOW MOLECULAR WEIGHT HAVING ANTICOAGULANT, ANTITHROMBINIC AND ANTITHROMOBIC ACTIVITY

[75] Inventors: Armando Cedro, Cislago; Roberto Porta, Cernobbio; Franco Cattaneo, Gorla Minore; Fabio Trento, Pare'; Laura Ferro; Ennio Lanzarotti, both of Milan, all of Italy

[73] Assignee: Crinos Industria Farmacobiologica S.p.A., Como, Italy

[21] Appl. No.: 08/993,172

[22] Filed: Dec. 18, 1997

[30] Foreign Application Priority Data

Dec. 18, 1996 [IT] Italy .................................. C096A0031

[51] Int. Cl.$^6$ .......................... A61K 31/715; C08B 37/00
[52] U.S. Cl. .......................... 424/115; 424/117; 424/123; 435/74; 435/101; 435/946; 514/54; 536/17.2; 536/54; 536/102; 536/118; 536/123; 536/124; 536/5
[58] Field of Search ..................... 424/115, 117, 424/123; 514/54; 536/5, 17.2, 102, 54, 118, 123, 124; 435/946, 74, 101

[56] References Cited

U.S. PATENT DOCUMENTS

| | | |
|---|---|---|
| B 408,030 | 1/1975 | Speakman . |
| 3,935,187 | 1/1976 | Speakman ................ 536/102 |
| 5,519,010 | 5/1996 | Fan et al. .................... 514/54 |

FOREIGN PATENT DOCUMENTS

| | | |
|---|---|---|
| 495 116 A1 | 7/1992 | European Pat. Off. . |
| 0 403 377 B1 | 12/1995 | European Pat. Off. . |

OTHER PUBLICATIONS

Patent Abstracts of Japan; vol. 10, No. 219; (C–363); Jul. 31, 1986.
Keiko Kitamura et al.; "Fucoidan from Brown Seaweed *Laminaria angustata* var. *longissima*"; Agricultural and Biological Chemistry, vol. 55, No. 2, 1991, pp. 615–616.
Takashi Nishino et al.; "Isolation, Purification and Characterization of fucose–containing sulfated polysaccharides from the brown seaweed *Ecklonia kurome* and their blood–anticoagulant activities." Carbohydrate Research vol. 186, No. 1, Feb. 15, 1989, pp. 119–129.
Springer G.F. et al.: "Isolation of anticoagulant fractions from crude fucoidin", Proc. Soc. Exp. Biol. Med. 1957 94 pp. 404–409.
T. Nishino et al.: "Isolation, purification and characterization of fucose–containing sulfated polysaccharides from the brown seaweed *Ecklonia kurome* and their blood–anticoagulant activities", Carbohyd. Res. 186, 119 1989.
H. Mori et al.: "Sugar constituents of some sulfated polysaccharide from the sporophylis of wakame (*Undaria pinnatifida*) and their biological activities", Mar. Algae Pharm. Sci. 2, 1982.
Nishino et al. "The Relationship Between the Molecular Weight and the Anticoagulant Activity of Two Types of Fucan Sulfates from the Brown Seaweed *Ecklonia kurome*", Agr. Biol. Chem. 55, 791 1991.
V. Grauffel et al: "New natural polysaccharides with potent antithromobic activity: fucans from brown algae", Biomaterials 10 363 1989.
S. Murray et al" Venous antithrombotic and anticoagulant activities of a fucoidan fraction", Thromb. and Haemost. 74(5) 1280 1995.
A. Nardella et al.: "Anticoagulant low molecular weight fucans produced by radical process and ion exchange chromatography of high molecular weight fucans extracted from the brown seaweed *Ascophyllum nodosum*", Carbohyd. Res. 289 (1996) pp. 201–208.
R. J. Winzler, Methods of Biochem. Anal. vol. 2 294 1955.
S. Colliec et al "Anticoagulant properties of a fucoidan fraction", Thromb. res. 64 142 1991.
"Heparin sodium", p. 737 U.S. Pharmacopeia XXIII, 1995.
T. Bitter, h. Muir, anal. Biochem. 4 (1962) 330–334.
P. Bacher et al. "The thrombolytic potency of LMW heparin compared to urokinase in a rabbit jugular vein lysis model", Thromb Res. 66, 1992, 151–158.
Reyers et al. "Statsis–induced venous thrombosis" in Standardization of animal models of thrombosis, 17th Angioloical Symposium Kitzbuhel—Proceedings K. Bredding, R. Zimmermann, F.K. Schattiner ed., Stuttgart 1983, pp. 99–104.
Reyers et al. "Failure at different doses of aspirin to modify experimental thromosis in rats", Throb. Res. 18, 1980, pp. 669–674.
W.A.P. Black et al. "Manufacture of algal chemicals IV–Laboratory scale isolation of fucoidin from brown marine algae", J.Sci. Food Agric. 3, 1952, pp. 122–129.
N. Volpi "Analytical techniques for studying structures of dermatan sulfate and low molecular weight heparin—Dermatan sulfate", 11 Farmaco, 47 (suppl. to n. 5) 1992, pp.841–853.

*Primary Examiner*—Herbert J. Lilling
*Attorney, Agent, or Firm*—Nikaido Marmelstein Murray & Oram LLP

[57] ABSTRACT

Fucans with low molecular weight having anticoagulant, antithrombinic and antithrombotic activity.

Fucan sulfates having molecular weight between 14000 and 29000 Dalton show a remarkable anticoagulant activity both in the global coagulation mechanism (APTT) and in the last phase of coagulation (antithrombinic activity). These compounds are useful also as antithrombotic drugs.

9 Claims, 2 Drawing Sheets

FUCANS WITH LOW MOLECULAR WEIGHT HAVING ANTICOAGULANT, ANTITHROMBINIC AND ANTITHROMOBIC ACTIVITY

The present invention relates to new fucans endowed with anticoagulant, antithrombinic and antithrombotic activity, their manufacturing process from brown algae or Phaeophycee, and their relevant formulations for parenteral, oral and topical use.

It has been known for several years that fucans extracted from brown algae are endowed of anticoagulant activity (Springer G. F. et Alii "Isolation of anticoagulant fractions from crude fucoidin" Proc. Soc. Exp. Biol. Med. 1957 94 404–9). The knowledge in this technical field has afforded to understand some aspects of the relationship between the structure and pharmacological activity of these substances. It has been established that anticoagulant activity is directly dependent on the sulfate content, and that besides it increases with decreasing uronic acid content (T. Nishino et Alii "Isolation, purification and characterization of fucose-containing sulfated polysaccharides from the brown seaweed Ecklonia kurome and their blood-anticoagulant activities, Carbohyd. Res. 186, 119 1989; H. Mori et Aiii "Sugar constituents of some sulfated polysaccharides from the sporophylls of wakame (*Undaria pinnatifida*) and their biological activities" Mar. Algae Pharm. Sci. 2.109 1982). Furthermore it has been found that both the coagulation time APTT and the thrombin time TT increase in fucan fractions with molecular weight between 10000 and 50000 Da (Nishino et Alii "The relationship between the molecular weight and the anticoagulant activity of two types of fucan sulfates from the brown seaweeds *Ecklonia kurome*" Agr. Biol. Chem. 55,791 1991). Other authors (V. Grauffel et Alii "New natural polysaccharides with potent antithrombotic activity: fucans from brown algae" Biomaterials 10 363 1989) have pointed out that for fucan preparations obtained from *A. nodosum, P. canaliculata e F. vesiculosus* the here above reported range is wider and extends from 18000 to 80000 Da. The latter compounds evidenced besides an antithrombinic activity (expressed in thrombin international units/mg of the compound) that depended on the molecular weight in the same way as anticoagulant activity. Hence the teachings of this art for both the pharmacological properties of fucans and the relationship between their structure and thereof pharmacological activities, indicate that the most active preparations are found among those having molecular weights lower than 80.000 Da, that have besides an high sulfur content. From this it can be understood the potential therapeutic interest of said fucans. For what concerns in particular their manufacturing processes in the literature of the field many have been described, which substantially correspond to two different approaches. In the one most followed, on the raw extract are performed subsequent fractionation steps, each exploiting a different physical property of said fucan polymers. The fractionation techniques usually employed are gel filtration, ion exchange chromatography, fractional precipitation effected by means of quaternary ammonium surfactants, or by addition of water-miscible organic solvents, such as ethanol or acetone. The second approach relies on methods of lowering molecular weight applied to high molecular weight fucans, i.e. substances more homogeneous from a chemical point of view than the raw extracts formerly hereabove mentioned. For what concerns the first approach it must be added that in the literature of the field it has been often observed that the number of steps required increases in a direct relation with the amount of pharmacological activity ought to be present in the final product. Suitable examples of this are provided by the two papers here below resumed. In S. Mauray et Alii "Venous antithrombotic and anticoagulant activities of a fucoidan fraction" Thromb. and Haemost. 74(5) 1280 1995, it was described a fucan isolated from *Ascophyllum nodosum* characterized as it follows from a chemical and physico chemical point: average molecular weight 20,000 Da, fucose 48.6%, uronic acids 5.8%, sulfur 9%. On the basis of the references therein given the relevant manufacturing process consisted of the following steps: (a) extraction in an aqueous media of the vegetal material (b) fractionation by means of quaternary ammonium salts (c) fractionation through column exclusion chromatography. The compound so obtained induced a significant lengthening of time both in APTT and TT tests, starting from a dose of 20 mcg/ml. In order to obtain the same APTT and TT values with heparin were required quantities by weight of said fucans amounting at 30–40 times that used for heparin. Besides this, by inspecting the values of $ED_{50}$ obtained in the thrombosis experimental model therein described it is drawn that the activity of said compounds was the same of that given by a quantity by weight of heparin 17 times lower. In the paper of T. Nishino et Alii Carbohyd. Res. 186 (1989) 119 (see above) it was described a manufacturing process consisting of the following steps: (a) extraction in boiling water of the dried and grounded powder of *Ecklonia kurome*, (b) precipitation with cetylpyridinium chloride and dissolution of the precipitate in 4 M NaCl, (c) precipitation by addition of ethanol and dissolution in water, (d) precipitation by means of calcium chloride, recovery of the supernatant and lyophilization, (e) ion exchange column fractionation and recovery of the fractions eluted by applying to the bed resin, 0.95 M NaCl and, respectively, 2 M NaCl solutions, (f) fractional precipitation performed on the collected solutions by addition of ethanol containing calcium acetate, (g) gel filtration chromatography. The two fucan preparations were characterised, respectively, by the following physico chemical and chemical parameters: molecular weight 32,000 and 21,000 Da, sulfur 14.6 and 13.3%, fucose 50.1 and 49.5%, uronic acids 1.5 and 3.9%, specific-rotation −142° and −129°. APTT and TT activities of said compounds evidenced an opposite trend. APTT titres, expressed in units/mg taking as the reference standard an heparin preparation assayed at 167 I.U./mg, were found to be 136 and 142 and hence quite near to the standard. TT titre was instead very low, amounting respectively at 13 and 11 I.U./mg. Said otherwise, said compounds are very active in inhibiting the global mechanism of coagulation, but scarcely effective in inhibiting thrombin, which is the enzyme involved in the last step of coagulation. For that it concerns the depolymerization methods, the European patent n.403,377 discloses methods for lowering molecular weight of fucans wherein as starting materials are employed fucans with an high sulfur content. The latter compounds are prepared by extracting the dried and grounded podwer of seaweeds in acidic conditions (HCl 0.01 N) in the presence of calcium chloride. The supernatant from the extraction is then neutralized and the solute recovered by precipitation with cetylpyridinium chloride. Depolymerization can be effected by chemical methods, by submitting the high molecular weight compounds to acidic conditions (1 N sulphuric acid) at a temperature of 45° C., or otherwise by means of specific enzymes contained in the raw extracts from *Haliotis tuberculata* or *Aplysia californica,* or alternatively, by gamma radiation using an overall dose of 11.5 Mrads. The compound obtained at the end undergo a gel filtration step in order to isolate the fraction having a molecular weight comprised between 13 and 23 KDa and a sulfur content from 7.8 to 11%. It can be drawn that the products of the invention must have a sulfur content higher in a percentage comprised between 2 and 20% than that of the starting fucan.

From the pharmacologic tests described in the European patent it is drawn that APTT titre (or kaolin-cephalin time) is very low since it is below 7 I.U./mg. From the tables of the description it is elicited that in order to obtain approximately the same thrombin time of heparin it is requested a quantity of fucan at least 15 times higher than that of the reference standard. Still about fucan depolymerization in another paper published in this field (S.Colliec et Alii "Anticoagulant properties of a fucoidan fraction" Thromb. Res. 64 143 1991) are given the results obtained in APTT and TT tests performed on a fucan preparation having an average molecular weight of 20,000, obtained by depolymerization in acidic conditions with the subsequent fractionation step performed as thaught in the aforesaid European patent. It is further referred that in order to obtain in said tests the same activity of heparin it was needed a quantity by weight of fucan 50 times higher. In the paper of A. Nardella et Alii "Anticoagulant low molecular weight fucans produced by radical process and ion exchange chromatography of high molecular weight fucans extracted from the brown seaweed *Ascophyllum nodosum*" Carbohyd. Res. 289 (1996) 201–208, it is described a radical depolymerization process, performed in the presence of hydrogen peroxide and cupric salts at a temperature of 60° C. for 5 hours, of two high molecular weight fucans, therein referred to as F1 and F2, having the following analytical data and pharmacological activities: preparation F1: sulfur 8.1%, fucose 31.3% , uronic acids 5.7% molecular weight 556,000 Da, APTT activity 9.1 I.U/mg; preparation F2: sulfur 5.7 %, fucose 35.8 %, uronic acids 11.6%, molecular weight 516, 000 Da, APTT activity 12.1 I.U./mg. The depolymerized product obtained from F1, identified in the paper as DF1 was characterized as it follows: sulfur 9.2%, fucose 36.4%, uronic acids 2.6%, molecular weight 8,300 Da, APTT activity 8.2 I.U./mg. The depolymerized product obtained from F2 (DF2) had a sulfur content of 9.3%, fucose 32.2%, uronic acids 6.5%, molecular weight 7,800 Da, APTT activity 7.3 I.U./mg.

From the prior art that hereabove it has summarized, the following conclusions can be drawn. In order to obtain fucan preparations of low molecular weight and high APTT activity, that could be useful as inhibitors of the coagulation cascade, the teachings of T. Nishino et Alii (see above) should be followed but thereof disclosed process for isolating said compounds is of little use for an industrial application. However it consists of several fractionation steps. On the other end if low molecular weight fucan preparations endowed with an higher thrombin inhibiting activity or antithrombinic activity (TT test) are requested, it is preferable to choose the depolymerization methods disclosed in the European patent n. 403,377. However, as it has been evidenced, APTT activity of the thereto obtained substances is quite low.

As a consequence of the above it is drawn that in the field of this art it remains still unsolved the problem of making available low molecular weight fucans to be used as anticoagulants, which show APTT and antithrombin activities more balanced between them and at the same time more comparable to those of heparin.

A first object of the present invention is the low molecular weight fucans obtainable by brown algae or Phaeophycee, endowed of a significant anticoagulant activity both as APTT activity/global mechanism of coagulation and as antithrombinic activity, and besides of a significant anti- thrombotic activity, characterized by the following chemical, physico-chemical and pharmacological parameters (data on a dry weight basis) sulfur 12.5–15%, fucose 43–57%, uronic acids 2–9%, molecular weight 14,000–29, 000 Da, specific rotation from −137° to 170°, APTT titre 40–80 I.U./mg, TT titre 18–30 I.U./mg. The fractions of low molecular weight fucan sulfate having sulfur content comprised between 14 and 15%, fucose 44–56%, uronic acids 2–3.5%, specific rotation between −160° and −170°, molecular weight 17,000–25,000 Da, APTT titre comprised between 60 and 80 I.U./mg and TT titre between 23 and 30 I.U./m.g, are preferred.

It has to be noted that the compounds of the present invention show the following differences versus those of the prior art:

the thrombin time is from 1.5 to 2.5 times higher compared to the low molecular weight fucan fractions disclosed in the paper of T. Nishino et Alii Carbohyd. Res. 186, 119 1989 (see above), APTT activity and sulfur content is higher than the corresponding of the substances disclosed in EP 403, 377.

A further object of the invention is the use of said compounds as medicaments, in particular as anticoagulant and antithrombotic agents.

Anticoagulant activity was demonstrated as APTT and TT activities according to the methods herein after reported.

APTT bioavailability versus heparin following subcutaneous administration was also investigated and found to be 20% for the reference standard calcium heparin (APTT titre 186 I.U./mg) and, respectively, of 39 and 40% for preparations VO264.A and VO264.B made according to the invention (see the examples). The claimed substances, compared on a weight basis to heparin, evidenced twice the bioavailability of calcium heparin. Hence the anticoagulant activity in vivo of the new fucans dosed in APTT units is of the same order of that obtained after heparin calcium administration.

Antithrombotic activity was demonstrated in the venous stasis thrombosis experimental model referred herein after. On assaying preparation VO246.B at the dose of 10 mg/Kg no thrombus was formed; in the same experimental conditions the minimum dose of calcium heparin (reference standard) which prevented thrombus formation was of 1 mg/Kg, i.e. only ten times lower.

The analytical methods used for the characterization of the fucans were the following ones.

Fucose determination was according to R. J. Winzler, Methods of Biochem. Anal. vol.2 294 1955, using as reference standard L (−) fucose.

Uronic acid determination was according to T. Bitter, H. Muir Anal. Biochem.4 (1962) 330, using as reference standard D(−) glucuronic acid.

Sulfur was assayed according to the ICP-AES (Inductively Coupled Plasma-Atomic Emission Spectometry) technique, using as the internal standard cobalt nitrate hydrate $Co(NO_3)_2, 6H_2O$, dissolved at a concentration of 1000 mg/l in 0.5 M $HNO_3$ (Merck catalogue n. 19785.0500), as a reference standard an aqueous solution containing a known quantity of sulfur (batch 302267E, C.A. 22831, Johnson Matthey-ALFA). By the aids of two burettes filled, respectively, with the solution of the reference standard of sulfur (solution A) and of the internal standard (solution B), were prepared in 5 different 100 ml volumetric flasks 5 solutions with a sulfur concentration of 100, 80, 60, 40 and 20 mg/l, by adding the following aliquots of solution A: 10 ml; 8 ml; 6 ml; 4 ml; 2 ml. In each volumetric flask was then added 0,8 ml of solution B. The five solutions were then brought to volume with distilled water.

The solution of the sample with the unknown sulfur content was prepared by weighing in a 100 ml volumetric flask about 60 mg. About 50 ml of distilled water were then added and mixing was effected until a clear solution was obtained. Before making up to volume with distilled water 0.8 ml of solution B were poured into the volumetric flask.

Determination of sulfur content in the samples was made by reporting on the calibration line obtained with the standard solutions, which has in abscissas the sulfur concentration in mg/l and on the ordinates the ratio between the intensity of sulfur emission, assayed at the wavelength of 182.037 nm, and that of the internal standard (cobalt), assayed at the wavelength of 222.616 nm, the reading obtained wiht the sample with unknown titre.

Molecular weight was determined by gel permeation chromatrography (GPC) performed on two columns connected in series, Supelco Progel TSK-G 4000 SW® and Supelco Progel TSK-G 3000 SW® having dimensions 30 cm×7.5 mm (with a precolumn progel TSK-SW® of dimensions 7.5 cm×7.5 mm) with refractive index detector. The buffer was 0.2 M sodium sulfate in water (28.4 g in 1000 ml). Flow rate was 0.5 ml/min and the injected volume of 50 microlitres. Molecular weight standards used in the assay were the following: maltoheptaose mol.wt. 1153 g/mole (Sigma® code n. M-7753), Dextran T-10 (Pharmacia Biotech® code n.17-0250-01) mol. wt. 10.000 ($M_W$), Dextran T-40 (Pharmacia Biotech® code n. 17-0270-01) mol. wt. 40.000 ($M_W$), Dextran T-70 (Pharmacia Biotech® code n.17-0280-01) mol.wt. 69.100 ($M_W$), Dextran T-500 (Pharmacia Biotech® code n. 17-0320-01) mol.wt.460.500 ($M_W$). 50 mg of each of the above compounds and of the sample were weighed in a 5 ml volumetric flask and dissolved in the elution solvent. The resulting solution was then brought to volume and filtered on a Millipore® membrane with pores of 0.22 μm. Calibration was effected starting from the solution with the highest molecular weight. Injection was repeated three times taking the average retention time. The sample was injected at the end and the corresponding retention time determined.

In this way a calibration line is made wherein it is then reported the average retention time obtained injecting the sample.

The average molecular weight (M) and the retention time (t) are related by the equation $\log M = At^3 + Bt^2 + Ct + D$. From the retention time of the fucan sulfate sample by using the calibration line it was then determined, by the aid of a software program, the average molecular weight of the sample.

Specific rotation was determined on a Perkin Elmer mod. 241 polarimeter, at the temperature of 20° C. at the sodium D line.

APTT titre, expressed as I.U/mg, was determined according to U.S. Pharmacopeia XXIII-1995 (rif. heparin sodium, page 737) using the Kit Hemodiagnostica Stago® art.n. 26551 and mutton plasma (DITTA Glo. Ros, Vercelli). Reference heparin was the international standard III (NIBSC—London). In the tests herebelow described were used the fucan sulfate preparations VO264.B and VO264.A and, as the reference compound, calcium heparin manufactured by the applicant (batch n.9, APTT titre 186 I.U./mg).

APTT activity biovailability of the preparations was determined by dividing the value of anticoagulant activity assayed after subcutaneous administration by that assayed for the same compound after intravenous administration. In both cases said values of activity had been calculated as the areas under the curve, obtained by plotting for each administration route APTT time (in the ordinates) against the times at which blood samples were taken from the animals (in abscissas). APTT tests were performed according to the instructions given in the package insert of the diagnostic kit above mentioned.

Figure 1:
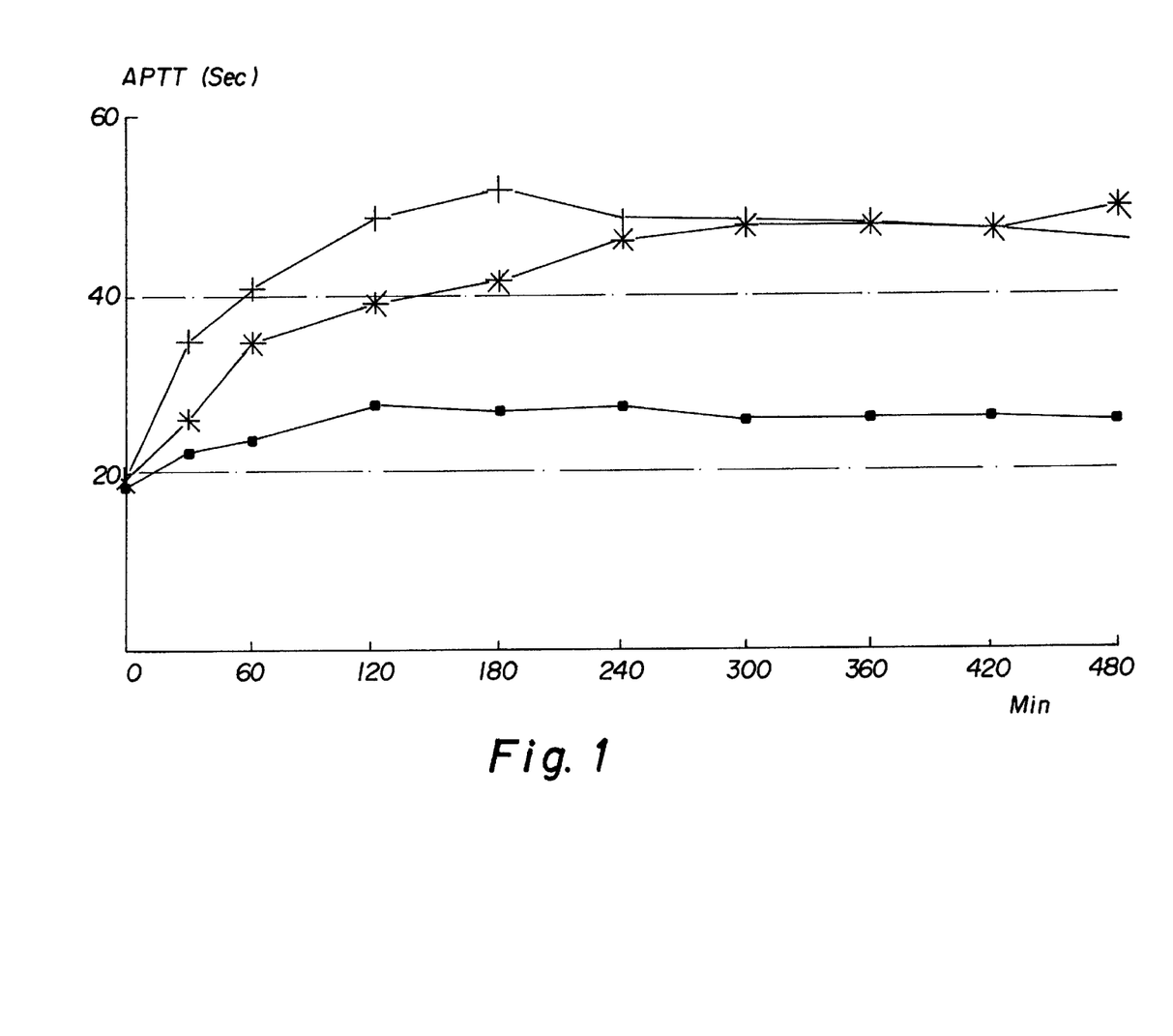
FIG. 1 shows APTT bioavaliabilty following subcutaneous administration of each of the following compounds: Preparation V0264.B: +, preparation V0264.A: *; calcium heparin: ■.

Delivery by subcutaneous administration was effected by dissolving in a physiologic solution the fucans of the invention at a concentration of 20 mg/0.2 ml. For calcium heparin a concentration of 4 mg/0.2 ml was used. For each of the compounds under test 4 rabbits (New Zealand White rabbits —Allevamento del Verbano di Conelli, Arona—Italy) were used. Administration by subcutaneous route was effected by injecting 0.2 ml/Kg of the above solutions in one point of the back of the animals previously shaved. Blood (2 ml) was taken from the marginal vein of the ear in basal conditions (time 0), then after 30 minutes, afterwards at 1 hour's intervals, continuing up to a total of 8 hours counted from the start of the experiment. As plasma anticoagulant agent a 3.8% sodium citrate solution was used, admixed with blood in a proportion 1 part citrate: 9 parts of blood. In FIG. 1 the curves given by each of the tested compounds are identified by the following symbols: preparation VO264.B : +, preparation VO264.A : * ; calcium heparin : ■. Experimental points of each curve were the average of four data. Activity was calculated from the area between each curve and the reference (dotted) line. The reference line, as seen from the figure, was parallel to abscissas and intersected the ordinates axis in the point corresponding to APTT basal value. FIG. 1 evidences that the bioavailability of the compounds of the invention had been systematically underestimated, as the areas thereto at the point corresponding to the time of the last blood sampling are not closed on the reference line.

Figure 2:
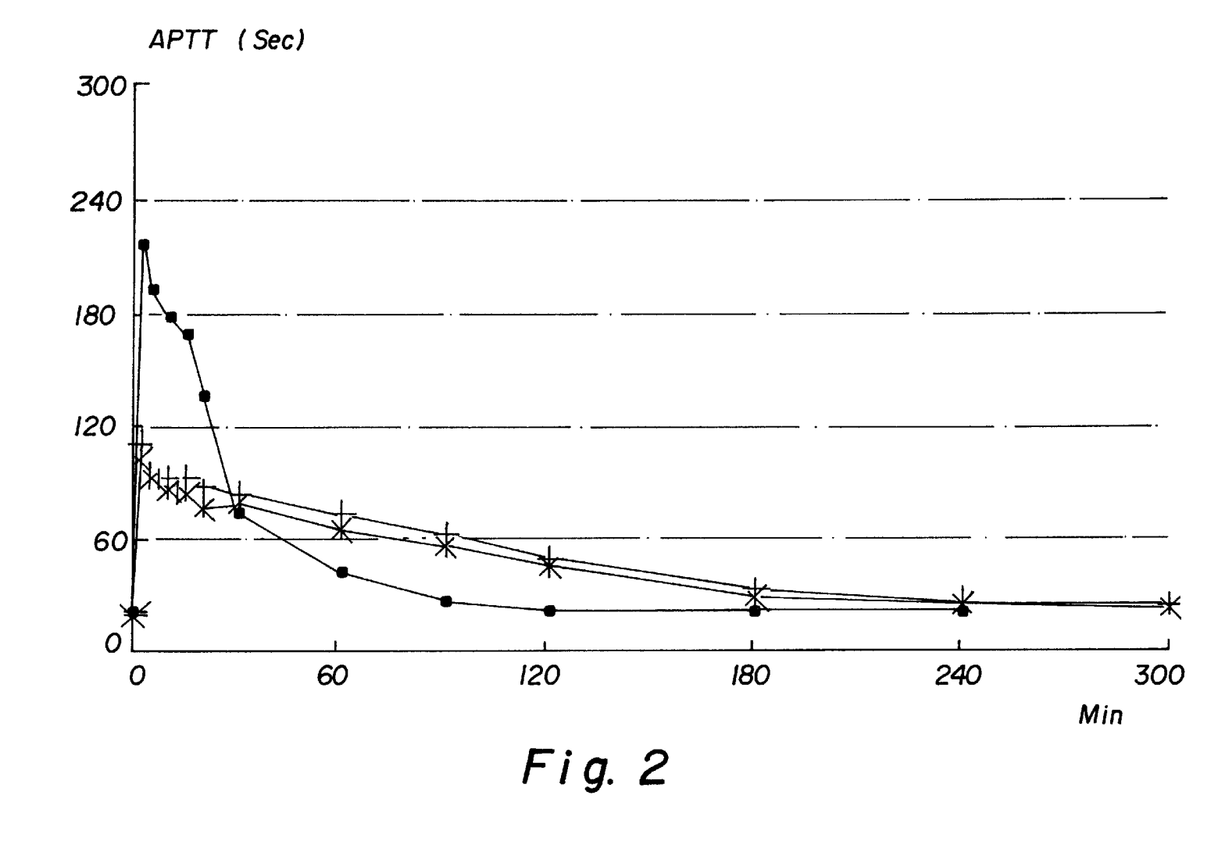
FIG. 2 shows APTT bioavailability following intravenous administration of each of Preparation VO264.B : + preparation VO264.A: *; calcium heparin: ■.

For assaying activity following intravenous administration were prepared solutions of the here above mentioned fucans at a concentration of 5 mg/ml, and for heparin at a concentration of 1 mg/ml. Each of said solutions was then injected (volume 1 ml/Kg) into the marginal vein of the ear of rabbits (n. 4 animals). Blood samples (volume 2 ml, added of an aliquot of the 3.8% sodium citrate solution in the same proportions here above referred to) were taken from the marginal vein of the other ear, in basal conditions and respectively at 2,5,10,15,20,30,60,90,120 minutes, then afterwards regularly at one hour's intervals. Plotting in a graph APTT values against time of blood sampling were obtained the curves of FIG. 2. The areas were calculated in the same way as formerly here above detailed. The meaning of the symbols featured on each of the three curves of FIG. 2 is the same as those of FIG. 1.

Biovailability of the test compounds was drawn from the area under the curve obtained, respectively, from the graph relevant to subcutaneous administration and that to intravenous administration, by applying the following formula:

$$\frac{\text{Area under curve}_{subcutaneous\ administration} \times 100}{\text{Area under curve}_{intravenous\ administration} \times 4}$$

Thrombin time (TT) expressed as I.U./mg, was determined by means of the Kit Hemodiagnostica Stago® art.n. 126594. The test was carried out according to the same procedure reported in the U.S. Pharmacopeia for the APTT test.

The experimental model of thrombosis from venous stasis was performed basically according to the following papers: P. Bacher et Alii "The thrombolytic potency of LMW heparin compared to urokinase in a rabbit jugular vein lysine model" Thromb. Res. 66,151–158 1992; I. Reyers et alii "Stasis-induced venous thrombosis" in Standardisation of animal models of thrombosis. 17th Angiological Symposium Kitzbuhel—Proceedings K. Breddin, R. Zimmermann, F. K. Schattiner editors, Stuttgart 1983, pages 99–104; I. Reyers et Alii "Failure at different doses of aspirin to modify experimental thrombosis in rats" Thromb. Res. 18, 669–674, 1980.

In a physiologic solution (volume 10 ml) were dissolved, respectively, the following compounds: calcium heparin (lot 9, manufactured by Crinos) at a concentration of 2 mg/ml and fucan sulfate preparation n. VO264.B at a concentration of 10 mg/ml. The animals (New Zealand White rabbits, Allevamento del Verbano di Conelli, Arona—Italy), were divided into 3 groups (4 rabbits/group) and after anesthesia underwent tracheotomy with following intubation. The tissues surrounding the right jugular vein were then carefully isolated for an overall length of 3 cm distally a ligature was effected to reduce blood flow. After 10 minutes an i.v. bolus of 1 ml/kg was administered through the ear marginal vein according to the following scheme:

control group: physiologic solution.
heparin-treated group: 2 mg/Kg.
VO264.B treated-group: 10 mg/kg.

5 minutes after the injection, uphill the ligature a curved hemostatic pincers was applied on the vein in order to produce an endothelial lesion of 2 cm length. Immediately after, distally was applied a second pincers for stopping completely blood flow. The curved hemostatic pincers was dislodged after 30 minutes. After 60 minutes the same was made for the second pincers. The ligature was instead left on the vein. The thrombus was recovered two hours after the start of the experiment, corresponding to one hour after the time when the second pincer had been removed. The thrombus was dried in an oven at 80° C. for 24 hours and weighed. Said experimental model of thrombosis represents quite closely what happens in real thrombosis pathology. In said model venous stenosis does not prevent completely blood flow in the vessel analogously to what happens in vivo when thrombus is formed. It is noted that in the hour following the removal of the second pincers thrombus may still grow since the initial stenosis, as said, allows some blood to flow.

A further object of this invention is a process to obtain the new low molecular weight polymers that comprises of the following steps:

a. extraction of the grounded and dried powder of algae with water at boiling or nearby (92–100° C.) temperatures under stirring for 16 hours. This step is known already from the paper of W.A.P. Black et Alii "Manufacture of algal chemicals IV. Laboratory scale isolation of fucoidin from brown marine algae " J. Sci. Food Agric. 3 1952 pages 122–129;

b. Filtration of the preceeding suspension, pH adjustment of the filtrate to a value within 2 and 2.5. At this point a precipitate constituted of a portion of the alginates that are contained in the extracted mass was formed. Said jelly-like solid was separated from the supernatant by filtration and the filtrate pH is adjusted to neutrality;

c. the supernatant solution was then concentrated to about ¼–⅕ of the starting volume in an ultrafiltration apparatus equipped with a membrane having a cut-off of 100,000 Da. In the same equipment the retentate was then dialyzed against 3 volumes of water and at the end it could be concentrated, if necessary, in order to reduce the final volume;

d. the raw extract was recovered from the retentate solution obtained at the end of the preceding step by precipitation after previous salting and subsequent addition of two volumes of ethanol or acetone;

e. the raw extract was then dissolved in an aqueous solution and the degradation and contemporary depolymerization of the compound was then effected in the presence of an inorganic cupric salt and hydrogen peroxide at a temperature of 55° C. By means of preliminary laboratory tests it was determined the reaction time needed in order to obtain a fucan having a molecular weight comprised between 14000 and 29000. The ratio, as percentage by weight between the cupric ion and the raw extract was of 1.3% and the ratio between the volume (ml) of hydrogen peroxide solution 8% w/v and the weight (g) of raw extract, was comprised between 5,5 and 36. The pH during the step was comprised between 6,0 and 7,5. (ref. U.S. patent B 408030 and in the paper of N. Volpi: "Analytical techniques for studying structures of dermatan sulfate and low molecular weight heparin—Dermatan sulfate " IL Farmaco, 47 (supplement to n.5) 841–853 1992);

f. at the end of the reaction the solution was filtered, a salt was added and precipitation of the solute was effected by adding two volumes of ethanol. The solute was then dehydrated and dried, recovering the corresponding mixed salt of sodium and copper II of the products according to the invention;

g. the compounds were then converted into the corresponding sodium salts by ion exchange treatment with a Na$^+$ resin. At this purpose the substances were dissolved in water at a concentration comprised between 5 and 7% and the resulting solution can be charged on a column containing the resin or can be added with the resin and thereof suspension stirred for the time needed the cation exchange to occur. The process could be monitored by means of a copper ion selective electrode. The ratio by volume between the bed resin and the solution varied from ½ to ⅔.

h. At the end filtration of the solution was effected, pH adjusted to a value within 6.0 and 6.5, salt was added to the solution and the compounds of the invention were precipitated by mixing with two volumes of ethanol, then recovering the sodium salt of the fucans according to the invention.

A further object of this invention is the raw extract obtainable from brown algae or Pheophycee by steps a.–d. of the above process and characterized by the following chemical, physico chemical and pharmacological parameters (data on a dry weight basis) : sulfur 6–8%, fucose 31–36%, uronic acids 23–27%, molecular weight 450, 000–800,000, APTT 40–60 I.U./mg.

With the process of the invention it is possible. to depolymerize the raw extract obtained after extraction from the vegetal material and removal of the alginates by acid precipitation. It is hence not needed the isolation of a more purified high molecular weight fucan as it happens according to the process disclosed in EP 403,377.

The applicant has shown (Example 6) that by depolymerizing a purified fucan having a molecular weight of 652.000 (APTT titre 67.5), obtained from the raw extract VO246.B, by means of sodium acetate/hydrogen peroxide for 24 hours, i.e. in the same conditions by which from the same raw extract are obtained preparations VO264.A and VO264.B (ref. examples 7 and 9 respectively), the low molecular weight (8800 Da) polymer that at the end was isolated had a very reduced pharmacologic activity (APTT titre 22.1 I.U./mg) compared to the preparations of this invention. This means that from a pure high molecular weight fucan cannot be obtained the products of the invention.

Worth noting is that the depolymerization methods available in the state of the art give different compounds when the raw extract isolated according to steps a)–d) of the process of the invention is therein used as starting material. By depolymerizing the raw extract in acidic conditions (pH 2.2 at 60° C. for 16 hours—ref. ex. 4) are obtained compounds containing a quantity of uronic acids higher than that of fucose. By depolymerizing the raw extract by gamma radiation (ref. ex. 5), were isolated compounds with a very low sulfur content and containing a large amount of degradation products. The compounds of the invention can be obtained only by lowering the molecular weight of the intermediate product in the presence of an inorganic cupric salt and of hydrogen peroxide (ex. 7).

A further object of this invention are the dosage forms or formulations containing as the active principle the low molecular weight fucans of the present invention. The latter can be used also in the form of their pharmacologically acceptable salts. Said formulations can be both for parenteral and oral administration.

Formulations for topical use (ref. ex. 16) may be also for non-pharmaceutical uses and have suitable composition for such a purpose.

Dosage forms for parenteral use may be sterile apyrogenetic solutions in sealed ampoules, or otherwise liophylizates contained in sealed bottles to be dissolved extemporarily in aqueous sterile solvents. As aqueous solvents can be used isotonic solutions made with conventional buffers (citrate, phosphates and the like) together with known preservatives. Oral formulations can be available in the form of tablets, coated tablets, gelatin capsules and granules.

Said dosage forms can be prepared according to known techniques. For instance, for that it concerns in particular oral dosage forms, they can be prepared with the usual techniques, for instance by direct compression of powders or granulates and may include binders, lubricants and disaggregating agents.

Dosage forms for parenteral administration may contain from 1 to 90 mg/ml of the 'active principle (for liophylizates the preceding figures must be referred to the final concentration of the compound in the sterile solvent), those for oral administration from 20 to 400 mg/unit dose.

Compositions for local topical use can be in the form of gels, creams, ointments, solutions containing from 0.1 to 20% by weight of the active principle.

Analytical data given in the following examples are calculated on dry weight basis.

The following examples are given for a better understanding of the invention and should not be considered to be a limitation thereof.

EXAMPLE 1

Extraction of the Raw Fucan Sulfate Preparation n.VO246.A 1 kg of *Fucus vesiculous* dry powder was suspended under stirring in 7 liters of distilled water in a reaction vessel of 15 liters equipped with a refrigerator. When the suspension was ready (about 15 minutes), at 100° C. for 16 hours on an oil bath heating was performed. The suspension was then cooled at 40° C. and centrifuged at 3000 r.p.m. for 20 minutes by using n. 4 1-liter centrifuging large test tubes. The jelly-like solid that remained at the bottom of said large test tubes was again suspended in water at the temperature of 60° C. under stirring for about 15 minutes. Centrifuging was effected again and then to the opalescent supernatant 200 mg of Clarcel FLO/MA® (grounded calcined perlite) was added. Upon filtration 6.3 liters were recovered and were added of 50 ml of HCl 37% in order to lower pH at a value of about 2.1. Centrifuging was effected again and the jelly-like solid (weight 44,4 g—preparation code n. 0195/95005-D—sulfur 0.7%, uronic acids 51%) was discarded and the supernatant brought to a neutral pH by adding a NaOH 30% solution. Concentration was then effected maintaining a constant volume of 1.5 liters in an ultrafiltration apparatus Amicon® CH2-A equipped with a 100.000 Dalton mol. wt. cut-off membrane-After the concentration step the solution was dialyzed on the same membrane, against 3 volumes of distilled water. The retentate (1,6 liters) was added of 112 g (7% w/v) of anhydrous sodium acetate and then stirred until an homogeneous solution was obtained. The solute was precipitated with 2 volumes of ethanol. After decanting overnight, the solid was dehydrated and dried. 79.68 g were at the end collected (yield about 8%) of a compound (preparation n.VO246.A) having the following analytical data on a dry weight basis: sulfur 6.5%, fucose 31.7%, uronic acids 23.8%, molecular weight 493,000 Da, APTT titre 53.4 I.U./mg, TT titre 18.2 I.U./mg.

Example 2

Extraction of the Raw Fucan Sulfate Preparation n.VO246.B.

In a 300 liter reaction vessel were poured 175 liters of distilled water. 25 Kg of *Fucus vesiculosus* dry powder were added and steam-jacket heating was effected in order to reach and maintain the temperature of 92° C. for 16 hours. At the end the temperature was lowered at 30° C. and 5 Kg of Clarcel FLO/MA® were added. Filtering was performed on a filter press apparatus equipped with Seitz K 800® cellulose filters. The filtrate was collected and the solid was dispersed in water (20 liters) at 60° C. under stirring, that afterwards was maintained for 1 hour. Filtering was effected again on Seitz K 800® filters and the filtrates were then united, yielding 220 liters as a whole. The solution was transferred into a reaction vessel, 5.5 kg of Clarcel CBR® (grounded calcined diatomite) were added, then cooled at 25–30° C., and precipitation was effected by lowering pH to 2 by addition of about 1.5 liters of HCl 37%. Stirring was then resumed and continued for 15 minutes and the slurry filtered on Seitz K 800® filters. The filter cakes were then washed with 20 liters of an acidic solution (pH 2) and the liquids collected at the end were in an overall volume of 220 liters. The solution was then charged into an ultrafiltration Alfa Laval® apparatus equipped with a mol. wt. cut-off 100,000 Millipore® cartridge. At first the solution was concentrated to reduce the volume to 50 liters, then dialyzed at a constant volume against 3 volumes of water. When the step was over the solution volume was further reduced to 25–30 liters. The solution was discharged from the apparatus, salted with NaCl up to a concentration of 2% w/v and 2 volumes of acetone were added. The resulting formed suspension was allowed to decant and then the precipitate was recovered, dehydrated, grounded and dried. 1665 g of raw extract batch n.VO246.B (yield 6.7%) were then collected. Thereof analytical data on a dry weight basis were the following: sulfur 7.1%, fucose 32.0%, uronic acids 25.0%, molecular weigh 800,000 Da, APTT titre 55 I.U./mg.

EXAMPLE 3
Extraction of the Raw Fucan Sulfate Preparation n. VO246.C.

The experimental procedure of the preceding example was repeated starting from 25 Kg of another batch of *Fucus vesiculosus*. pH of the intermediate precipitation in this case was of 2.5. 2100 g (yield 8,4%) of preparation VO246.C. were obtained, characterized by the following analytical data: sulfur 7.6%, fucose 35.8%, uronic acids 26.1%, molecular weight 470,000 Da, APTT titre 44 I.U./mg.

EXAMPLE 4
Depolymerization in Acidic Conditions of the Raw Fucan Sulfate Preparation VO246.B.

5 g of VO246.B were dissolved in 500 ml of distilled water in a 1 l volumetric flask, connected to a refrigerator. 10 ml of HCl 1 N were added in order to lower pH to 2.2 and heating was effected in an oil bath at 60° C. for 16 hours. At the end the solution was cooled, pH was corrected to 7 with a NaOH solution. The liquid was dialyzed in an Amicon® CH2-A ultrafiltration equipment at a constant volume, in three consecutive steps, against 5 volumes of distilled water each time. In the first phase (step A) the dialysis membrane used had a 3000 Da mol.wt. cut-off. In the second (step B) the membrane had a 10,000 Da mol.wt. cut-off and in the third (step C) of 100.000 Da. The solutes of the permeates of step A, B and C, were precipitated after concentration of the solutions by evaporation under reduced pressure and salting with NaCl up to a salt concentration 2% w/v and following addition of two volumes of acetone. Three different fractions were thus collected each weighing, respectively, 57 mg (preparation 0195/95026-A), 6,5 mg (preparation 0195/95026-B), that was afterwards discarded, and 496 mg (preparation 0195/95026-C).

Uronic acids and fucose analysis gave the following results: preparation 0195/95026-A uronic acids 38.0%, fucose 8.9%; preparation 0195/95026-C uronic acids 20.1%, fucose 21.2%.

The retentate coming from the last dialysis step (step C) was salted with NaCl up to a salt concentration 2% w/v and the solute precipitated with 2 volumes of acetone. 2,4 g (preparation 0195/95026-D) were obtained which contained 32.5% of uronic acids and 16.25% of fucose.

EXAMPLE 5
Gamma Ray Depolymerization of the Raw Extract VO246.B 1.5 g of the raw extract were dissolved in a 150 ml volumetric flask in phosphate buffer 0.1 M pH 7, bringing to volume after the substance had dissolved. Said solution was then distributed in n. 5 30 ml vials, that were then hermetically sealed and sent to the firm Gammaton (Guanzate-Como) for the gamma ray treatment. n. 2 vials were treated with a 2,5 Mrad gamma radiation and the other two with 20 Mrad. For each of the two treated samples one vial was taken and added of NaCl up to a concentration 2% and the solute precipitated with two volumes of acetone.

From the solution treated with 2.5 Mrad were obtained 460 mg of a compound (preparation 0195/96041-A) having a phosphate titre of 51% w/w of the substance. The weight of the contained raw extract was hence of 225 mg, with a yield of 75% calculated on the starting raw extract. Analytical data calculated on the pure compound were as it follows: sulfur: 5.1%; uronic acids 16.1%, fucose 19.3%, molecular weight 38.500 Da.

The weight of the product recovered from the solution treated with 20 Mrad gamma radiation (prep. 0195/96041-D) was of 211 mg with a phosphate content of 71% w/w of the substance. As a consequence of that the real weight of the contained raw extract was of 61.2 mg (yield of 20% on the starting raw extract). The analytical data were as it follows (ref. to the pure compound): sulfur 5.55% uronic acids 3.38%, fucose 5.79%, molecular weight 5600 Da.

EXAMPLE 6
Preparation of a Purified High Molecular Weight Fucan Sulfate (Preparation n.VO248.A) and Following Depolymerization for 24 Hours in Copper Acetate in the Presence of Hydrogen Peroxide (Preparation VO269.A)

200 g of raw extract preparation n.VO 246.B were dissolved in 10 liters of water. 200 g of NaCl were then added and stirring was effected until an homogeneous solution was obtained. 7.5 liters (0.75 volumes) of acetone were added and then left overnight. The precipitate was collected and after dehydration and drying were obtained 126.5 g. To the supernatant were then added 12.5 liters of acetone (2 volumes of the solvent as a whole), recovering 68.3 g of purified fucan sulfate (preparation n. VO248.A) having the following analytical profile: sulfur 8.9%, fucose 48.5%, uronic acids 9.7%, molecular weight 652.000 Da, specific rotation −112.8°, APTT titre 67.5 I.U./mg.

10 g of the compound obtained were dissolved in 200 ml of distilled water. The solution was transferred into a vessel and then heating by means of an oil bath at 55° C. was effected under stirring. 400 mg of cupric acetate monohydrate were added and after solution pH was corrected to 7.5 by means of a few drops of 1 N NaOH.

By means of a peristaltic pump the 8% w/v hydrogen peroxide solution at a flow rate of 2.3 ml/h was added. Reaction time was of 24 hours and pH between 6.0 and 6.5 (overall volume added of hydrogen peroxide: 55 ml). Filtration was then effected on Seitz K 800® filters, recovering 400 ml of a clear solution, which was added of 28 g of anhydrous sodium acetate and then of two volumes of ethanol. The gummy-like precipitate was dissolved into 70 ml of distilled water, to which were added 30 ml of Amberlite® IRC 718 resin ($Na^+$ form) and left for 6 hours under stirring. The solution at the end appeared colorless—slightly opalescent, and it was filtered on a sintered glass filter after addition of 10 g of Clarcel CBR®. pH was brought to 6.5 by addition of some drops of glacial acetic acid, the solution was then salted with anhydrous sodium acetate up to a concentration 7% w/v and the solute precipitated with two volumes of ethanol. After dehydration and drying were recovered 2.90 g of the depolymerized product (preparation VO 269.A—yield 29%) containing 12.9% of sulfur, fucose 53.2%, uronic acids 2.5%, molecular weight 8.800 Da, specific rotation −14.8°, APTT titre 22.1 I.U./mg.

EXAMPLE 7
Depolymerization of the Raw Extract VO246.B with Copper Salts for Different Times to Yield Preparations VO260.A, VO264.A and 0195/96044-C.

50 g of VO246.B were dissolved in 1 liter of water. The solution was heated at the temperature of 55° C. and 2 g of copper acetate monohydrate were added, adjusting pH to 7.5 with NaOH 1 N. At this stage, by means of a peristaltic pump calibrated on a flow rate of 46 ml/h, an 8% w/v solution of hydrogen peroxide was added, maintaining pH between 6 and 6.5 by means of NaOH 30% solution. After 6 hours ⅓ (425 ml) by volume of the solution was taken out, salted with anhydrous sodium acetate up to a concentration 5% w/v and 2 volumes of ethanol were added. The precipitate thus obtained (9 g) was dissolved in water to a concentration 5% w/v (180 ml) and applied to a column filled with resin Amberlite® IRC 718 (Na+ form), having a bed of about half the volume of the water used to dissolve the residue. The flow rate was of 40 ml/h. The column eluate was salted with anhydrous sodium acetate and precipitation was afterwards effected with ethanol according to the procedure here above reported already. 7.0 g (yield 42%) of a preparation batch n.VO260.A were obtained, having the following analytical features: sulfur 9.9%, fucose 38.3%, uronic acids 15.1%, molecular weight 88,500 Da, specific rotation −119.6°, APTT titre 58.1 I.U./mg, TT titre 14.8 I.U./mg.

After 24 hour the solution volume was of 2 liters. 1 liter was taken out and underwent to the same steps here above described by which preparation VO260.A. was obtained, yielding 2.6 g (yield 15.6%) of preparation batch n. VO 264.A having 14.5% of sulfur, fucose 56.2%, uronic acids 2.3%, molecular weight 22,500 Da, specific rotation—1650, APTT titre 74.9 I.U./mg, TT titre 23 I.U./mg.

On a further aliquot of the remaining depolymerization solution, addition of hydrogen peroxide went on for further 24 hours (total depolymerization time 48 hours). At the end the solution was processed as the two aliquots here above mentioned, wherein in this case solution pH was adjusted to 6.7, by means of concentrated acetic acid, immediately before ethanol precipitation. 1 g (yield 6.2%) of the preparation batch n. 0195/96044-C were obtained. The compound was characterized by the following analytical parameters: sulfur 15%, molecular weight 9,700 Da. APTT titre 23.6 I.U./mg, TT titre 6.7 I.U./mg.

EXAMPLE 8
Depolymerization for 6 Hours of the Raw Fucan Preparation VO246.C. and Isolation of the Preparation VO260.C.

200 g of the compound were dissolved in 4 liters of distilled water. According to a preliminary test performed conformingly to the method disclosed in preceding example 6, it was assessed that the reaction time was of 6 hours. The solution was heated at 55° C. and under agitation were added 8 g of copper acetate monohydrate. pH was adjusted to 7.5 by addition of about 8 ml of NaOH 30% solution. At this point an hydrogen peroxide solution 8% w/v was added with a flow rate of about 183.3 ml/h (1,1 liters as a whole). During the reaction pH was maintained at a value between 6.5 and 7.0 by suitable addition of small quantities of NaOH 30% solution. At the end sodium acetate trihydrate was added to the solution up to a concentration of 11% w/v, and afterwards two volumes of ethanol. The precipitate was collected, dehydrated and dried. 79 g of a solid were thus collected, that afterwards were dissolved in 1.2 liters of distilled water. Centrifuging at 3000 r.p.m. was then effected in order to clear away at least in part the turbidity of the solution. 800 ml of Amberlite® IRC 718 (Na+ form) was added and the slurry was left under stirring overnight. The solution was recovered and the resin washed with two volumes of distilled water. Filtration was then effected on a buckner funnel, on which were formerly layered 15 g of Clarcel CBR®, obtaining a clear solution which volume was of about 2.8 liters and pH of 8.9. pH was then adjusted to 6.5 by addition of a few drops of glacial acetic acid. Afterwards anhydrous sodium acetate was added up to a concentration of 7% w/v and precipitation was effected by adding two volumes of ethanol. After dehydration and drying 60,1 g (yield 30,1%) of preparation VO260.C. were obtained, having the following analytical profile:
sulfur 12.6%, fucose 47%, uronic acids 8.1%, molecular weight 29,000 Da, specific rotation −138.20, APTT titre 49.6 I.U./mg, TT titre 21 I.U./mg.

EXAMPLE 9
Depolymerization of Raw Fucan Sulfate Preparation VO246.B with Copper Salts for 24 Hours and Isolation of Preparation VO264.B.

100 g of VO246.B were dissolved in 2 liters of water. According to a preliminary test performed conformingly to the method disclosed in preceding example 6, it was assessed that the reaction time was of 24 hours. 4 g of cupric acetate monohydrate were added. pH was corrected to 7.5 with NaOH 30% and then heated at 55° C. By means of a peristaltic pump a 8% w/v solution of hydrogen peroxide was added (flow rate 45.8 ml/h) keeping the pH between 6 and 6.5. After 24 hours the quantity by volume of $H_2O_2$ solution added was of 1100 ml. The final solution appeared very opalescent and it was centrifuged. The supernatant was added of anhydrous sodium acetate up to a concentration 7% w/v. The solute was precipitated with 2 volumes of ethanol, dehydrated and dried. 23.25 g were recovered that were dissolved in 400 ml of water. 260 ml of Amberlite® IRC 718 (Na+ form) resin were added and stirring was started and continued overnight. Filtration was then effected on a sintered funnel, washing afterwards said filter with 100 ml of distilled water. The filtrate pH was adjusted to 7 by adding acetic acid, anhydrous sodium acetate up to a 7% w/v concentration was added followed by two volumes of ethanol. After dehydration and drying 16.4 g of a solid (preparation VO264.B—yield 16.4%) were obtained. The following analytical features were found: sulfur 14.3%, fucose 44.2%, uronic acids 3.4%, molecular weight 17,500 Da, specific rotation −168.6°, APTT titre 69.5 I.U./mg, TT titre 28 I.U./mg.

EXAMPLE 10
Depolymerization with Copper Salts for 48 Hours of the Raw Extract VO246.C. and Isolation of Preparation VO267.A.

200 g of the raw extract were dissolved in 4 liters of distilled water. According to a preliminary test performed conformingly to the method disclosed in preceding example 6, it was formerly assessed that the reaction time was of 48 hours. Heating at 55° C. was effected and were then added, under stirring, 8 g of copper acetate monohydrate. pH was adjusted to 7.5 with about 8 ml of an NaOH 30% solution. At this stage a 8% w/v hydrogen peroxide solution was added at a flow rate of 23 ml/h (1,1 liters as a whole). pH during reaction was maintained between 6.0 and 6.5 by adding a small quantity of NaOH 30% solution. After 48 hours filtration was performed by using Seitz K 800® filters. Sodium acetate trihydrate was added up to a concentration of 11% w/v and the solute was then precipitated by adding two volumes of ethanol. The gummy-like residue was dehydrated and dried yielding 57.5 g. It was redissolved in 900 ml of distilled water and 600 ml of Amberlite® IRC 718 resin (Na+ form) were added. The slurry was left under stirring overnight. Filtration was made by means of a sintered funnel and the resulting solution was filtered again through the same funnel on which a bed of Clarcel CBR® has formerly layered. pH was adjusted to 6.5 by addition of a few drops of concentrated acetic acid, anhydrous sodium acetate was added to give 7% w/v concentration and the solute precipitated with two volumes of ethanol. The solid (preparation VO267.A) was collected, dehydrated and dried giving g 42.8 (yield 21.4% on the raw extract). Analysis of the compound gave the following results: sulfur 14.2%, fucose 49.8%, uronic acids 5.3%, molecular weight 14,700 Da, specific rotation—139.6°, APTT titre 45 I.U./mg, TT titre 19 I.U./mg.

EXAMPLE 11
Depolymerization of Raw Fucan Sulfate VO246.A for 18 Hours and Isolation of Compound VO246.A/1.

50 g of the compound VO246.A were dissolved in water. According to a preliminary test performed conformingly to the method disclosed in preceding example 6, it was assessed that the reaction time was of 18 hours. pH during the reaction was maintained between 7.0 and 7.5 by addition of small amounts of a NaOH 30% solution. It was then followed the procedure of example 6, by adding the same quantities of copper acetate and of hydrogen peroxide solution 8% w/v (overall volume added 2775 ml). 11.5 g of a compound (VO246.A/1) having the following analytical profile were obtained: sulfur 14.8%, fucose 49.3%, uronic acids 2.1%, molecular weight 25,000 Da, specific rotation −162°, APTT titre 27 I.U./mg.

In the examples 12–15 here below reported, which disclose formulations both for pharmaceutical uses and non, by the expression "low mol.wt.fucan sulfate" is meant a preparation of fucan sulfate falling within the instant limits of this invention.

EXAMPLE 12
Formulation for Subcutaneous Administration

| | |
|---|---|
| low mol. wt. fucan sulfate | 20 mg |
| bidistilled water | 0.2 ml |

EXAMPLE 13
Formulation for i.v. Administration

| | |
|---|---|
| low mol. wt. fucan sulfate | 80 mg |
| bidistilled water | 4 mg |

EXAMPLE 14
Preparation for Oral Use (Tablet)

| | |
|---|---|
| low mol. wt. fucan sulfate | 180 mg |
| mannitol | 300 mg |
| saccharose | 240 mg |
| polyvinylpyrrolidone | 14 mg |
| magnesium stearate | 9 mg |

EXAMPLE 15
Composition for Local Topical Use
Gel

| | |
|---|---|
| low mol. wt. fucan sulfate | 12 g |
| isopropanol | 25 g |
| 1,2 propylenglycol | 0.7 g |
| triethanolamine | 1.2 g |
| carbopol | 1.1 g |
| perfumes and bidistilled water enough to | 100 g |

Cream

| | |
|---|---|
| low mol. wt. fucan sulfate | 18 g |
| polyoxyethylenglycol stearate | 11 g |
| cetylstearyl alcohol | 14 g |
| propylenglycol | 9 g |
| perfumes, preservatives and bistilled | |
| water enough to | 100 g |

Aqueous lotion

| | |
|---|---|
| low mol. wt. fucan sulfate | 7 g |
| glycerine | 7 g |
| ethyl alcohol | 10 ml |
| perfumes, preservatives and bidistilled | |
| water enough to | 100 g |

EXAMPLE 16
Other Formulations for Topical Use
Aqueous Lotion for Cosmetic Use

| | |
|---|---|
| low mol. wt. fucan sulfate | 0.5–5 g |
| propylene glycol | 1.5 g |
| ethyl alcohol | 15 ml |
| perfumes, preservatives and bistilled | |
| water enough to | 100 g |

Emulsion with detergent activity

| | |
|---|---|
| low mol. wt. fucan sulfate | 4 g |
| PEG 15 glyceryl ricinoleate | 14 g |
| polysorbate 21 | 7 g |
| almond oil | 3 g |
| perfumes and bidistilled | |
| water enough to | 100 g |

We claim:

1. Fucan sulfates with low molecular weight obtainable from brown algae or Pheophycee having a significant anticoagulant activity both as APTT activity/global mechanism of coagulation and as antithrombinic activity, and besides of a significant antithrombotic activity, characterized by the following chemical, physico-chemical and pharmacological parameters (data on a dry weight basis): sulfur: 12,5–15%, fucose 43–57%, uronic acids 2–9%, molecular weight 14000–29000 Da, specific rotation from −130° to −170°, APTT titre 40–80 I.U./mg, TT titre 18–30 I.U./mg.

2. Fucan sulfates according to claim 1 characterized by the following chemical, physico-chemical and pharmacological parameters (data on a dry basis): sulfur 14–15%, fucose 44–56%, uronic acids 2–3,5%, specific rotation from −160° to −170°, molecular weight 17,000–25,000 Da, APTT titre 60–80 I.U./mg, TT titre 23–30 I.U./mg.

3. Fucan sulfates according to claim 1 obtained from *Fucus vesiculosus*.

4. Fucans according to claim 1 for use as medicaments.

5. A therapeutic composition comprising a therapeutically effective amount of fucans according to claim 4 and a pharmaceutical acceptable carrier.

6. The composition of claim 5 wherein the pharmaceutical carrier is acceptable for subcutaneous administration.

7. A process for obtaining the fucans of claim 1 comprising the following steps:
   a. subjecting a ground and dried powder of algae to an extraction procedure with water at boiling or near boiling temperatures with stirring for 16 hours to obtain a suspension in water;
   b. filtering the suspension in water to obtain a filtrate and adjusting the pH of the filtrate between 2 and 2.5, separating the formed precipitate by filtering and adjusting the pH of the supernatant to neutrality; to obtain a solution;
   c. concentrating the solution to about ¼–⅕ of the starting volume in an ultrafiltration apparatus equipped with a membrane having a cut-off of 100,000 Da, subsequently dialyzing against 3 volumes of water and, optionally, concentrating the solution;
   d. recovering a raw extract from the dialyzed, optionally concentrated solution by precipitation after salting and addition of two volumes of ethanol or acetone;

e. degrading and depolymerizing the raw extract obtained in the preceding step in aqueous solution in the presence of an inorganic cupric salt and 8% w/v hydrogen peroxide at a temperature of 55° C. and of a pH between 6.0 and 7.5, for the time needed to obtain a compound having a molecular weight comprised between 14000 and 29000, the weight ratio between the cupric ion and the raw extract of 1.3% and the ratio between the ml of 8% of hydrogen peroxide used and the grams of raw extract comprised between 5.5 and 36;

f. filtering and salting of the aqueous solution and precipitating the solute by adding two volumes of ethanol obtaining a precipitate of a mixed salt of sodium and copper II fucans;

g. dissolving the precipitate in water and treating with an ion exchange Na+ resin obtaining an alkaline solution; and h. filtering and adjusting the pH of the alkaline solution to a value within 6.0 and 6.5, salting of the solution and precipitating the fucans by adding two volumes of ethanol.

8. Raw extract obtainable from brown algae or Pheophycee by steps a.–d. of the process according to claim 7, characterized by the following chemical, physico chemical and pharmacological parameters (data on a dry weight basis): sulfur 6–8%, fucose 31–36%, uronic acids 23–27%, molecular weight 450,000–800,000, APTT 40–60 I.U./mg.

9. The composition of claim 5 wherein the pharmaceutical carrier is acceptable for parenteral, oral or topical administration.

* * * * *

UNITED STATES PATENT AND TRADEMARK OFFICE
CERTIFICATE OF CORRECTION

PATENT NO. : 5,948,405
DATED : September 7, 1999
INVENTOR(S) : Armando Cedro

It is certified that error appears in the above-identified patent and that said Letters Patent is hereby corrected as shown below:

On the title page, item [54] and column 1:
Change: "ANTITHROMOBIC" to --ANTITHROMBOTIC--.

Signed and Sealed this

Eighteenth Day of April, 2000

Attest:

Q. TODD DICKINSON

*Attesting Officer*   *Director of Patents and Trademarks*